(12) United States Patent
Rubens et al.

(10) Patent No.: US 10,883,579 B2
(45) Date of Patent: Jan. 5, 2021

(54) OSCILLATING MECHANISM FOR A POWER TOOL

(71) Applicant: Robert Bosch GmbH, Stuttgart (DE)

(72) Inventors: Jeremy Rubens, Palatine, IL (US); Jaime Moreno Terrazas, Imperial, CA (US)

(73) Assignees: Robert Bosch Tool Corporation, Broadview, IL (US); Robert Bosch GmbH, Stuttgart (DE)

(*) Notice: Subject to any disclaimer, the term of this patent is extended or adjusted under 35 U.S.C. 154(b) by 784 days.

(21) Appl. No.: 15/103,989

(22) PCT Filed: Dec. 4, 2014

(86) PCT No.: PCT/EP2014/076645
§ 371 (c)(1),
(2) Date: Jun. 13, 2016

(87) PCT Pub. No.: WO2015/091012
PCT Pub. Date: Jun. 25, 2015

(65) Prior Publication Data
US 2016/0290453 A1 Oct. 6, 2016

Related U.S. Application Data

(60) Provisional application No. 61/918,749, filed on Dec. 20, 2013.

(51) Int. Cl.
*F16H 21/52* (2006.01)
*B27B 19/00* (2006.01)
(Continued)

(52) U.S. Cl.
CPC .......... *F16H 21/52* (2013.01); *B24B 23/04* (2013.01); *B24B 27/08* (2013.01); *B24B 47/12* (2013.01);
(Continued)

(58) Field of Classification Search
CPC ......... B24B 23/04; B24B 27/08; B24B 47/12; B24B 47/16; B24B 27/065; B27B 19/006;
(Continued)

(56) References Cited

U.S. PATENT DOCUMENTS 2,639,620 A * 5/1953 Bamford ................. F16H 23/04
74/60
3,091,851 A * 6/1963 Cummins ............... A61F 15/02
30/264
(Continued)

FOREIGN PATENT DOCUMENTS

EP 0 631 843 A1 1/1995
EP 1 882 538 A2 1/2008

OTHER PUBLICATIONS

Wikipedia Article on Races of Bearings; p. 2 (Design section); relevant portion published Apr. 30, 2008.*
(Continued)

*Primary Examiner* — Dariush Seif
(74) *Attorney, Agent, or Firm* — Maginot, Moore & Beck LLP

(57) ABSTRACT

An oscillating power tool includes a drive motor (M) producing rotary motion and an oscillating mechanism (30) for converting the motor rotary motion to an oscillatory side-to-side movement. The oscillating mechanism (30) includes a link (32) driven by an eccentric shaft (16) of the motor (M), a drive arm (40) that drives the hub (45) of the working tool (B) in oscillating motion, and a bearing arrangement (37) between the drive arm (40) and the link (32) that isolates relative rotation and translation between the components while still imparting an oscillatory motion to the drive arm (40).

17 Claims, 8 Drawing Sheets

(51) Int. Cl.
  *B24B 23/04* (2006.01)
  *B24B 47/12* (2006.01)
  *B24B 27/08* (2006.01)
  *B26B 7/00* (2006.01)
  *A61B 17/14* (2006.01)

(52) U.S. Cl.
  CPC .............. *B26B 7/00* (2013.01); *B27B 19/006* (2013.01); *A61B 17/142* (2016.11); *B27B 19/008* (2013.01)

(58) Field of Classification Search
  CPC ....... B27B 19/008; F16H 21/52; F16H 21/16; F16H 23/00; B26B 7/00; A61B 17/142
  USPC .......................................... 173/100; 74/22 R
  See application file for complete search history.

(56) References Cited

U.S. PATENT DOCUMENTS

| | | | | |
|---|---|---|---|---|
| 3,337,952 A * | 8/1967 | Rosen | ................ | B23D 49/006 30/277.4 |
| 3,680,934 A * | 8/1972 | Laussermair | ........... | F16C 19/26 384/564 |
| 4,026,196 A * | 5/1977 | Olofsson | .................. | F04B 1/02 92/140 |
| 4,436,163 A * | 3/1984 | Simpson | ................ | A01G 3/053 173/109 |
| 4,922,612 A * | 5/1990 | Greenwood | ............ | A61F 15/02 30/166.3 |
| 4,978,235 A * | 12/1990 | Jacob | ................. | F16C 11/0614 384/450 |
| 5,295,749 A * | 3/1994 | Takahashi | ............. | F16C 23/086 384/568 |
| 5,533,925 A * | 7/1996 | Sato | ....................... | B23Q 5/027 451/163 |
| 5,555,626 A * | 9/1996 | Fuchs | .................... | B23D 51/16 30/392 |
| 5,566,458 A * | 10/1996 | Bednar | ................ | B23D 49/162 173/178 |
| 5,846,244 A * | 12/1998 | Cripe | ................. | B27B 19/008 606/82 |
| 6,109,791 A * | 8/2000 | Metton | ................. | F16C 19/466 384/569 |
| 7,104,873 B1 * | 9/2006 | Borinato | ................. | B24B 23/03 451/121 |
| 8,397,832 B2 * | 3/2013 | Blickle | ................. | B24B 23/028 173/109 |
| 9,700,949 B2 * | 7/2017 | Wang | .................... | B23D 51/16 |
| 2003/0051352 A1 * | 3/2003 | Clark, Jr. | ............... | B23D 49/11 30/392 |
| 2004/0103490 A1 * | 6/2004 | Long | .................... | A47L 11/125 15/22.1 |
| 2008/0027449 A1 * | 1/2008 | Gundlapalli | ........ | A61B 17/1613 606/82 |
| 2008/0184569 A1 * | 8/2008 | Moreno | .............. | B23D 49/165 30/392 |
| 2010/0270046 A1 * | 10/2010 | Schlesak | ............. | B25D 11/062 173/109 |
| 2011/0017483 A1 * | 1/2011 | Baumann | ............ | B25D 11/062 173/162.2 |
| 2013/0037290 A1 * | 2/2013 | Clabunde | ................ | B25F 5/006 173/162.1 |
| 2013/0048327 A1 * | 2/2013 | Machida | .............. | B25D 11/062 173/162.2 |
| 2013/0181414 A1 * | 7/2013 | Haman | ................. | B27B 19/006 279/144 |
| 2013/0269963 A1 * | 10/2013 | Fuchs | ................. | B23D 61/006 173/162.1 |
| 2014/0018811 A1 * | 1/2014 | Mootien | ............... | B27B 19/008 606/82 |
| 2014/0020918 A1 * | 1/2014 | Klabunde | ............. | B23D 47/12 173/49 |
| 2014/0068952 A1 * | 3/2014 | Soreo | .................... | B27B 19/008 30/369 |
| 2014/0190716 A1 * | 7/2014 | Sugiura | .................. | B24B 23/04 173/46 |
| 2015/0252844 A1 * | 9/2015 | Vance | ..................... | F16C 17/18 384/322 |

OTHER PUBLICATIONS

New Hampshire Ball Bearings (NHBB), (Jan. 16, 2013) (Year: 2013).*
International Search Report corresponding to PCT Application No. PCT/EP2014/076645, dated Feb. 18, 2015 (5 pages).

* cited by examiner

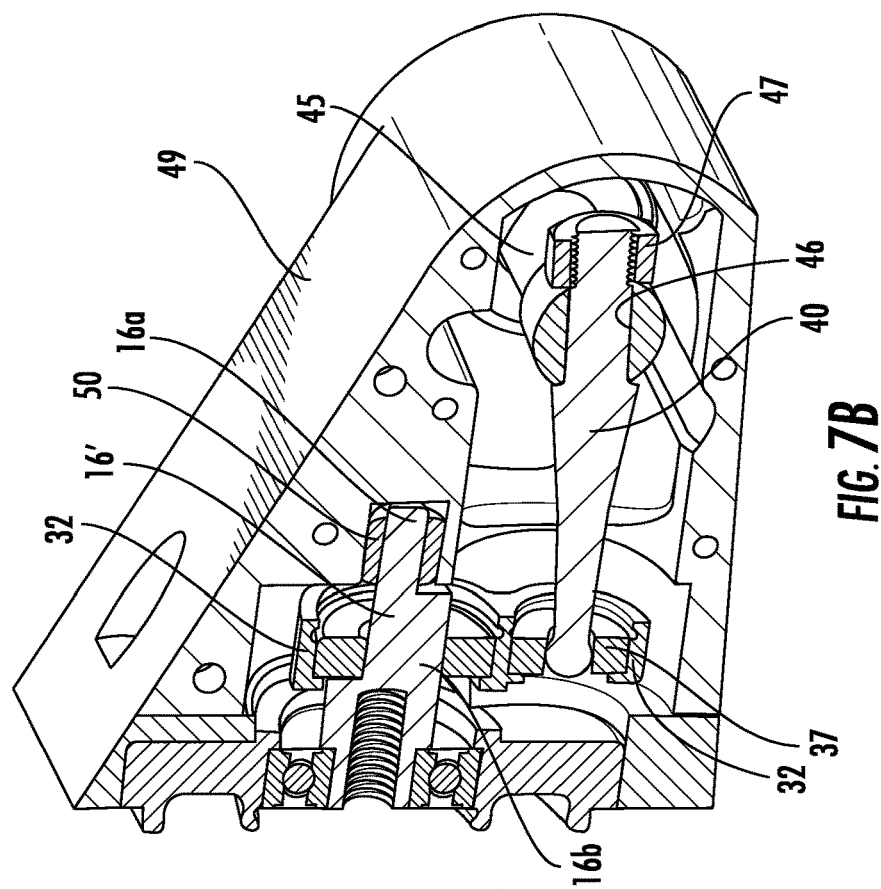
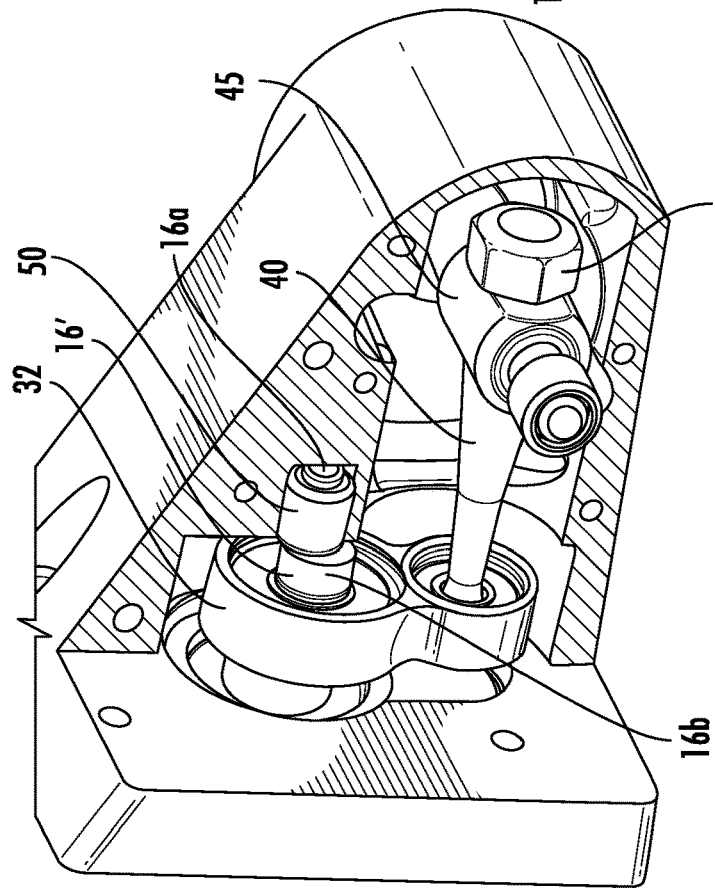

OSCILLATING MECHANISM FOR A POWER TOOL

REFERENCE TO RELATED APPLICATION AND PRIORITY CLAIM

This application is a 35 U.S.C. § 371 National Stage Application of PCT/EP2014/076645, filed on Dec. 4, 2014, which claims the benefit of priority to provisional application No. 61/918,749, filed on Dec. 20, 2013, the entire disclosures of which are incorporated herein by reference.

FIELD

This invention relates to the field of power tools, and more particularly to a handheld power tool having an oscillating tool or blade.

BACKGROUND

Oscillating power tools are lightweight, handheld tools configured to oscillate various accessory tools and attachments, such as cutting blades, sanding discs, grinding tools, and many others. The accessory tools and attachments can enable the oscillating power tool to shape and contour workpieces in a many different ways.

FIG. 1 illustrates the operating end of a conventional oscillating power tool 10 having a generally cylindrically shaped housing 12 and a tool holder 14, or tool head, located at a front end of the housing. The tool holder 14 is adapted to accept a number of different tools or tool accessories, such as a scraping tool or cutting blade, for instance. The tool holder 14 is configured to oscillate the tool from side to side by way of a reversing angular displacement about an axis A that is generally perpendicular to the longitudinal axis L of the tool housing. The housing 12 can be constructed of a rigid material such as plastic, metal, or composite materials such as a fiber reinforced polymer. The housing 12 can include a nose housing (not shown) to cover the front of the tool, the tool holder, and the oscillating mechanisms.

The housing 12 includes a handle portion formed to provide a gripping area for an operator. The housing 12 is further configured to carry a power supply and a motor M that drives a motor drive shaft 15 that has an eccentric drive portion 16 that is coupled to an oscillating mechanism 18 and more particular engages a spherical drive bearing 20 disposed between the arms 23 of a yoke 22. The rotation of the motor shaft produces a translation of the spherical bearing 20 which in turn produces a lateral translation of the yoke 22. The bearing 20 must be spherical to "release" the rotational degree of freedom between the bearing and yoke. Consequently, the contact between the spherical bearing and the yoke is essentially a point contact on each arm 23. Since the rotational degree of freedom is released between the components there is relative movement and sliding occurring at the interface, which leads to significant heat build-up and wear. The sliding at this interface also generates a moment in the bearing 20 that introduces a load in the direction of the longitudinal axis L.

The interface between the spherical bearing 20 and the yoke 22 also releases the X-direction translation parallel to the axis A since the eccentric drive portion 16 drives the bearing up and down. The yoke 22 is locked in this degree of freedom. In theory, the spherical bearing would roll at the X-direction interface, but testing has revealed that the bearing is only intermittently contacting the two arms 23 of the yoke 22 and is constantly changing the rolling direction and constantly sliding. This sliding movement generates heat which eventually damages the bearing.

Moreover, since the interface between the spherical bearing 20 and the yoke 22 releases the up and down motion in the X-direction, some clearance is required between the bearing and yoke arms. This clearance causes banging as the bearing impacts the yoke, thereby producing an impact load that further reduces the life of the bearing.

It can be seen that the conventional oscillating mechanism has a deleterious impact on the life of the spherical bearing 20. The sources of this weakness includes: a) the point contact between the spherical bearing and the yoke arms; b) sliding of the outer race of the bearing due to the relative rotation between bearing and yoke; c) up and down sliding of the bearing; and d) banging or impacting of the bearing due to necessary looseness of the bearing-yoke interface. Robustness, or more accurately, lack of robustness limits the size of blade and the operating conditions of the conventional oscillating tool, which can ultimately limit cutting performance. A larger blade increases the load on the oscillating mechanism 14 which consequently increases the load on the spherical bearing 20. An increase in operating speed also increases the bearing load. This increased load ultimately requires that limits be placed on the size and operating speed of the tool. Consequently, there is a need for an oscillating mechanism that overcomes these problems and allows for higher "power" and performance operation of an oscillating tool.

BRIEF DESCRIPTION OF THE DRAWINGS

FIGS. 7a-7b are cut-away views of an oscillating mechanism similar to the mechanism of FIGS. 2-4 with a bearing supporting the eccentric motor drive shaft.

DETAILED DESCRIPTION

Figure 1:
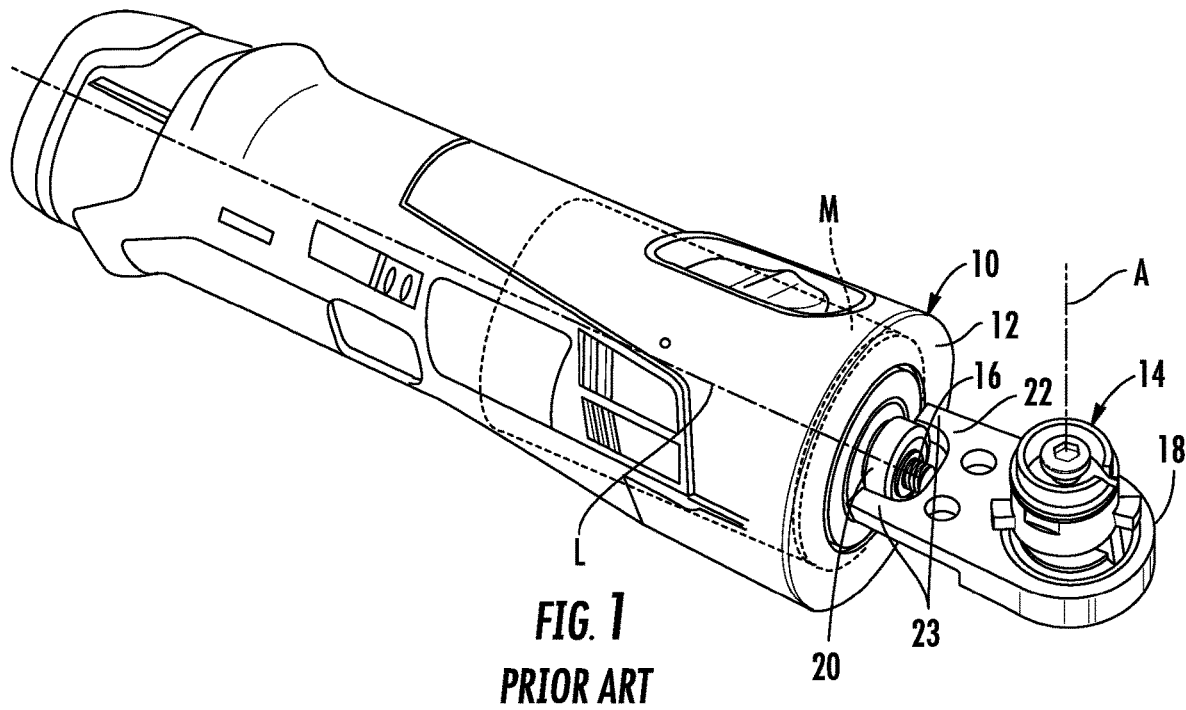
FIG. 1 is a perspective view of an oscillating power tool including an oscillating mechanism.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure encompasses any alterations and modifications to the illustrated embodiments and includes further applications of the principles of the disclosure as would normally occur to one of ordinary skill in the art to which this disclosure pertains.

Figure 2:
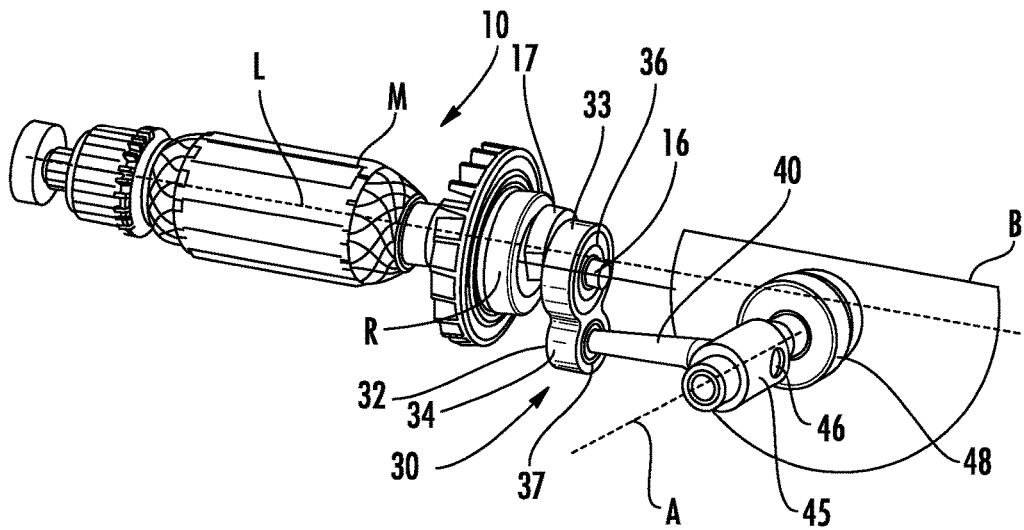
FIG. 2 is a perspective view of the drive components and oscillating mechanism for an oscillating power tool according to one aspect of the present disclosure.
Figure 3:
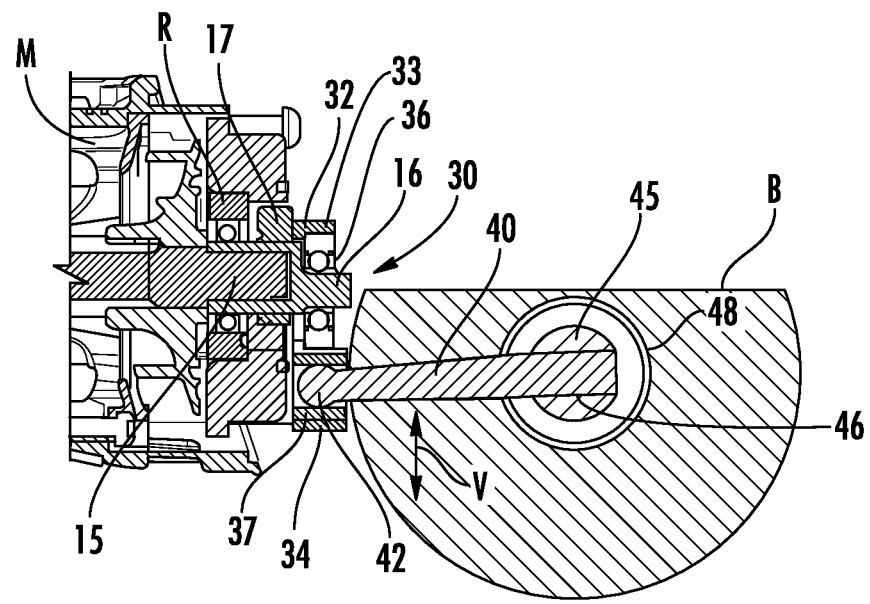
FIG. 3 is an enlarged side cross-sectional view of the drive components and oscillating mechanism shown in FIG. 2.
Figure 4:
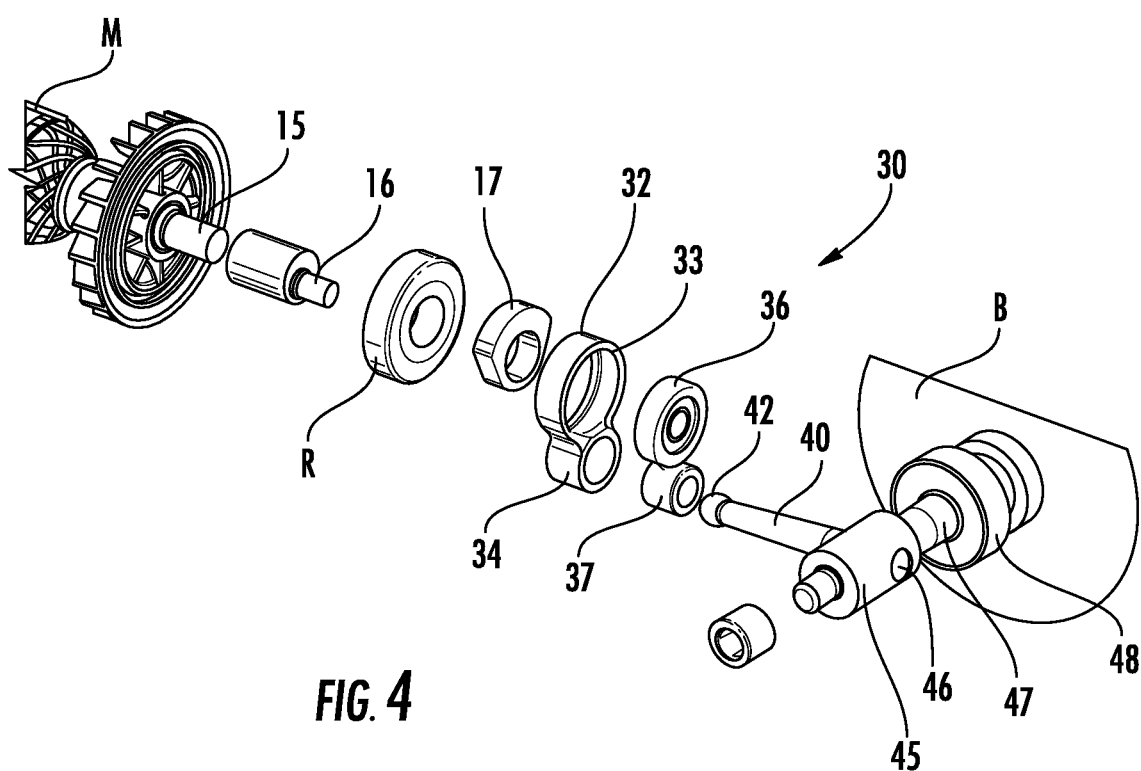
FIG. 4 is an exploded view of the drive components and oscillating mechanism shown in FIGS. 2 and 3.

In order to address the problems of the conventional oscillating power tool discussed above, the present disclosure contemplates an articulating mechanism that eliminates the point contact and sliding movement aspect of the prior oscillating mechanism. An articulating mechanism 30 shown in FIGS. 2-4 is coupled between the eccentric drive portion 16 of the motor M and an oscillating working tool or blade B. The eccentric drive portion 16 may be supported by a roller or other suitable bearing R disposed within the housing 12 of the tool. In one aspect, the oscillating mechanism 30 includes a link 32 having a first link housing 33 and a second offset link housing 34 that is offset below the first housing 33 relative to the longitudinal axis L. A counterbalance 17 may be mounted to the motor drive shaft 15 or the eccentric portion 16 at a position 180° opposite the second link housing 34. The counterbalance 17 has a mass generally equal to the mass of the second link housing 34 to balance the inertial force generated by eccentric rotation of the second link housing. The counterbalance thus reduces the lateral load on the drive bearing M supporting the eccentric drive portion 16. It is noted that no counterbalance is required for the first link housing 33 since that housing is aligned with the longitudinal axis L and does not generate any inertial force.

The first link housing 33 is configured to support a bearing 36 through which the eccentric drive portion 16 passes. The bearing 36 may be a conventional roller bearing to accommodate the rotation of the drive shaft within the link housing 33. The second or offset link housing 34 is configured to receive a second bearing 37. However, the second bearing 37 is configured to release relative rotation between the second offset link housing 34 and a drive arm 40. The drive arm 40 thus terminates in a spherical end 42 that is seated within the second bearing 37. The second bearing may thus be in the form of a low-friction bushing or other bearing interface that releases rotation between the two components. As best seen in the cross-sectional view of FIG. 3, the spherical end 42 of the drive arm 40 is in a close running fit within the second bearing 37 and is permitted to rotate about the axis of the spherical end 42 as well as to translate along the axis of the second link housing 34. The interface between the spherical end and the bearing thus also releases relative translation between the drive arm 40 and the offset link housing 34. The configuration of the bearing and spherical end of the drive arm thus limits the force transmission between the eccentric shaft and the drive arm to the vertical direction V.

The drive arm 40 is coupled to a hub 45 and shaft 47 that is supported for rotation by a bearing support 48. The shaft 47 is coupled to the working tool B so that rotation of the hub and shaft produces the desired oscillation of the working tool. The drive arm 40 is thus fixed to the hub 45 such as by engagement within a bore 46. The end of the arm may be threaded and engaged by a nut 47, as illustrated in FIGS. 7a-7b. It can be appreciated that as the drive arm 40 moves up and down in the direction V shown in FIG. 3 this motion pivots the hub 45 and thereby oscillates the tool B. The up and down movement V of the drive arm 40 is accomplished by up and down movement of the link 32 in the same direction V that occurs as the eccentric motor shaft 16 rotates. The eccentric movement of the eccentric shaft 16 causes the link 32 to not only move up and down in the direction V but also side-to-side in a direction parallel to the direction A (FIG. 2). However, since the interface between the drive arm 40 and the link 32 is a spherical interface the side-to-side movement is isolated from the drive arm. Moreover, the spherical end 42 is free to translate within the offset second link housing 34 to further isolate all rotation and translation other than the up-and-down movement V.

One significant benefit of the oscillating mechanism 30 is that there is no point contact between a bearing and any component of the mechanism. The first bearing 36 may be a conventional roller bearing or similar bearing. The second bearing 37 may be a bushing. Although the component engaging the surface of the second bearing 37 is the spherical end 42 of the drive arm 40, the interface is a line contact around the circumference of the spherical end 42. Even as the components wear and the running fit becomes more loose, there is no significant risk of banging or impacting between the spherical end 42 and second bearing 37 because the continuous rotation of the offset link housing 34 will maintain constant pressure on the spherical end as the housing tries to move the spherical end in the eccentric rotation pattern.

Figure 5:
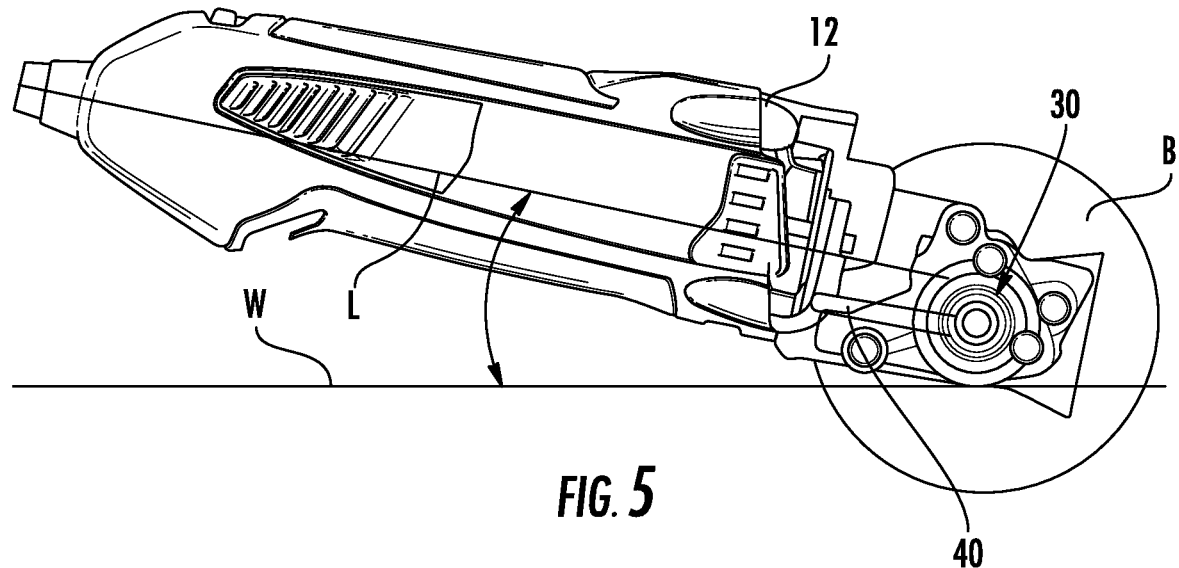
FIG. 5 is a side view of a power tool with a circular saw blade using the oscillating mechanism shown in FIGS. 2-4.
Figure 6:
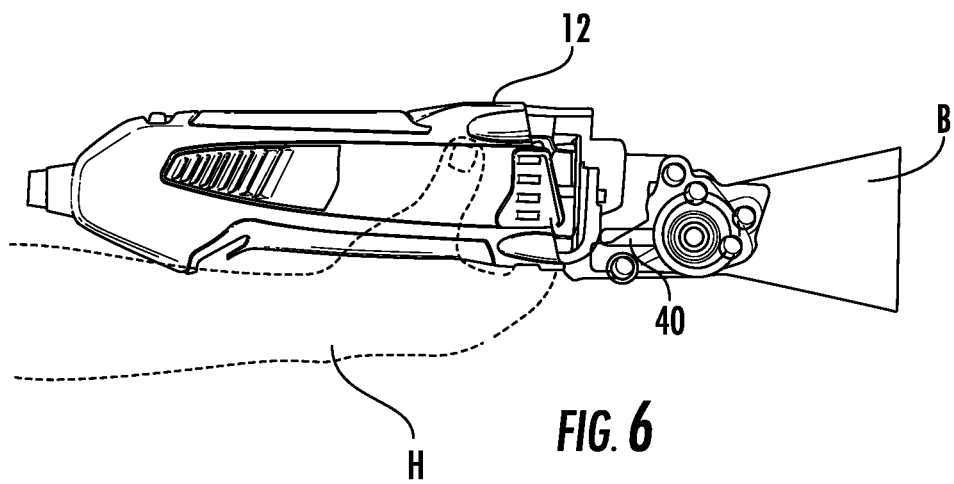
FIG. 6 is a side view of a power tool with an alternative oscillating blade using the oscillating mechanism shown in FIGS. 2-4.

Additional benefits are illustrated in FIGS. 5 and 6. As shown in FIG. 5, when the working tool B is a circular saw, the oscillating mechanism 30 allows the motor to remain on the longitudinal axis L of the tool 10 which is axially offset from the blade B. This feature allows the tool to be used at a sharper angle relative to the work surface W and allows the blade B o cut more deeply into the work surface. When the working tool B is a blade configured as shown in FIG. 6, the oscillating mechanism 30 allows the blade B to be generally in line with the operator's hand H when used in a standard oscillating orientation. This improves the overall ergonomics of the tool and reduces wrist strain for the operator.

The oscillating mechanism 30 may be modified as shown in FIGS. 7a-7b. The mechanism shown in these figures is the same as the mechanism in FIGS. 2-6 with a modification to the support for the motor drive shaft 15 and eccentric drive portion 16'. A housing 49 may be provided to surround the oscillating mechanism components, with the housing 49 fastened to the tool housing 12. This housing may be configured to support a bearing 50 that receives the end portion 16a of the eccentric shaft 16'. This bearing supports the drive shaft to eliminate any moment created by the link 32 cantilevered on the end of the shaft. Whereas in the embodiment of FIGS. 2-6 the link 32 is supported on the eccentric end of the shaft 16, in the embodiment of FIGS. 7a, 7b, the end portion 16a is aligned along the longitudinal axis to support the motor drive shaft. The shaft 16' further defines an eccentric portion 16b that engages the link 32 to impart the eccentric movement upon rotation of the shaft.

Figure 8:
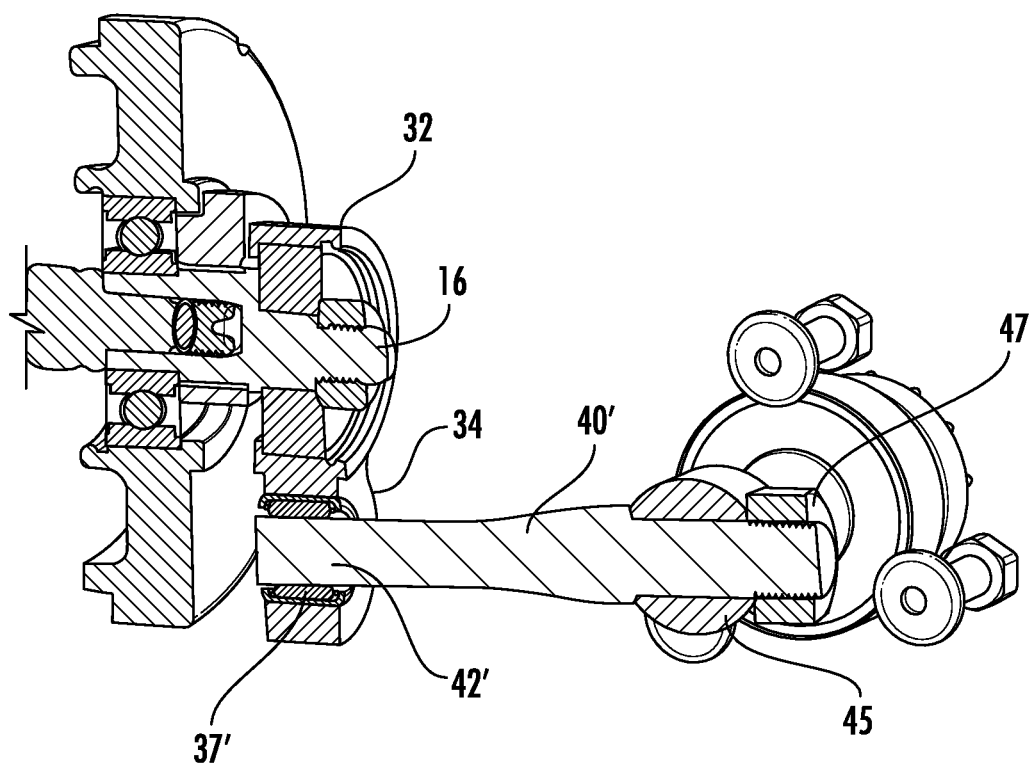
FIG. 8 is a representation of an oscillating mechanism according to another aspect of the present disclosure.
Figure 8A:
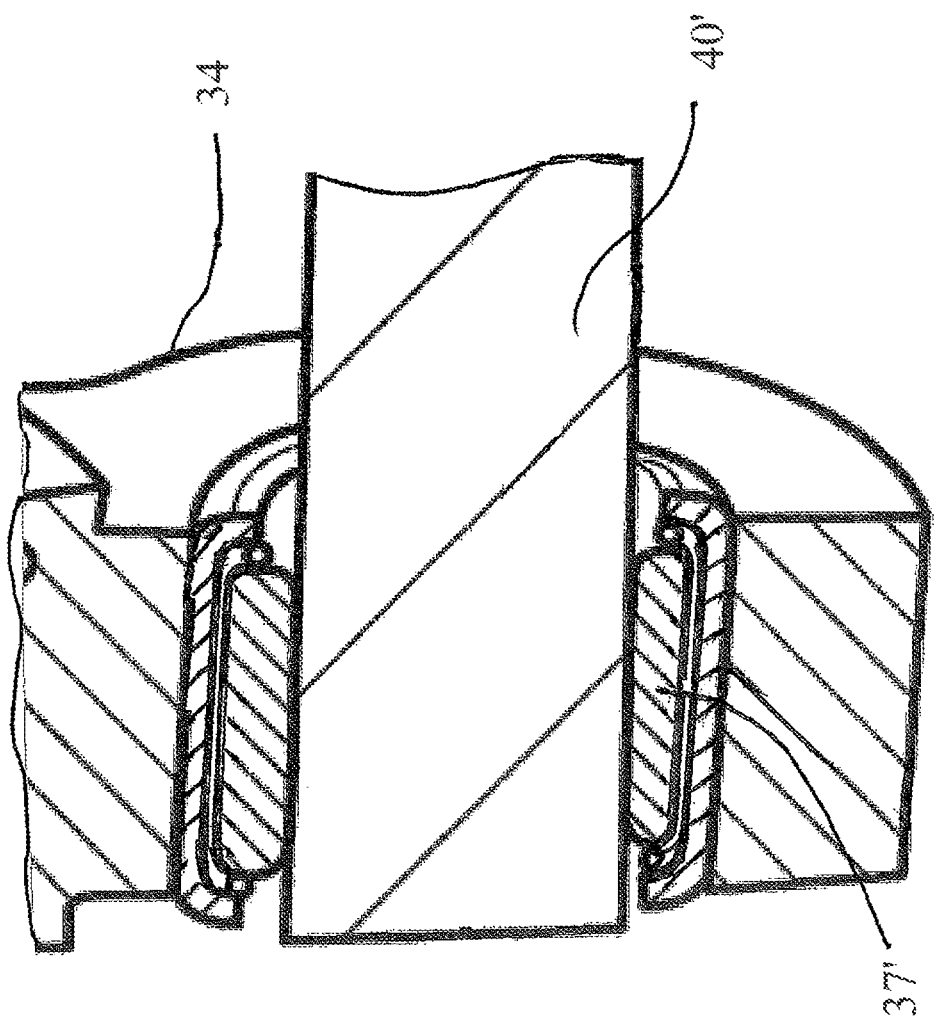

In a further modification shown in FIG. 8, the offset link housing 34 receives a bearing 37' that allows a certain amount of "slop" between the bearing and the end 42' of the drive arm 40'. The end 42' does not include the spherical configuration in this embodiment. Instead, the "slop" in the modified bearing 37' essentially simulates a spherical joint by allow a certain amount of play in the transmission of movement from the bearing 37' to the drive arm 40'. In certain applications, the drive arm 40' only rotates through an angle of ±3 degrees. The modified bearing 37' may be a roller bearing that incorporates a loose fit with a small amount of play between the inner race and the rollers, and/or between the rollers and the outer race. This alternative configuration allows the use of low cost standard components for the second bearing 37' without sacrificing functionality and performance.

Figure 9:
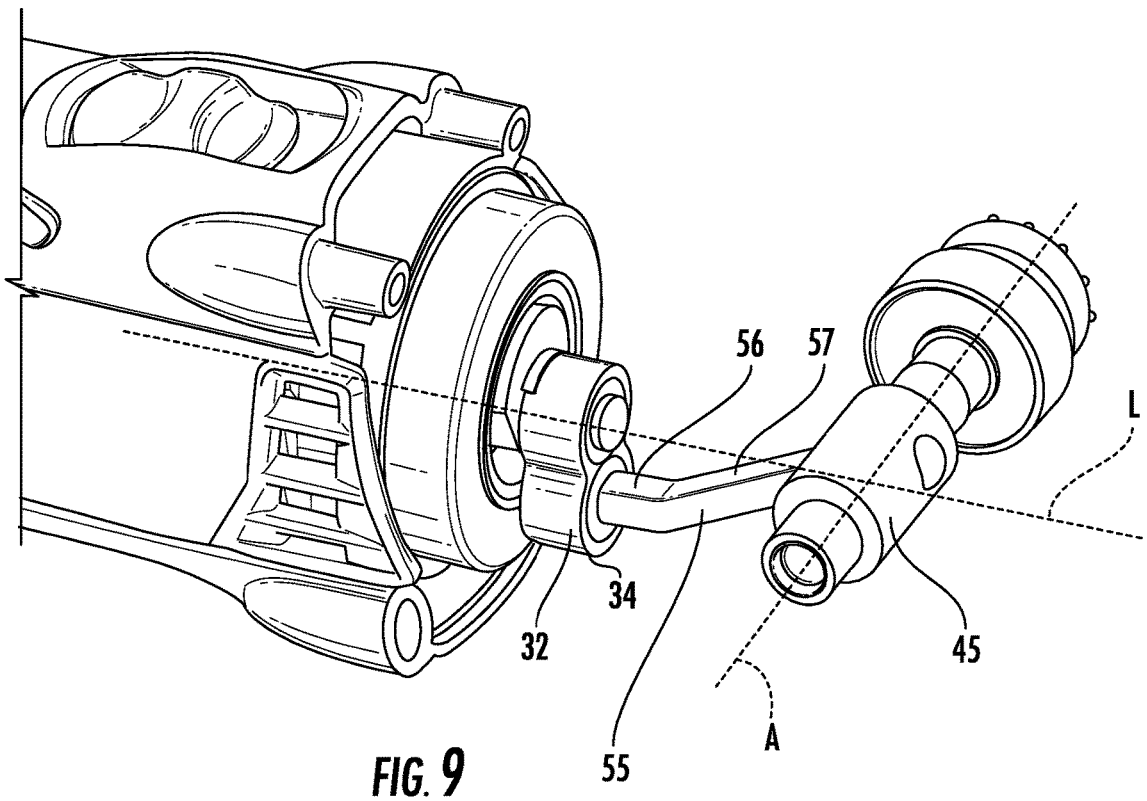
FIG. 9 is a representation of an oscillating mechanism according to a further aspect of the present disclosure.

Another modification is shown in FIG. 9. In this embodiment, the oscillating mechanism is similar to the mechanism 30 and link 32 except that the drive arm is modified. In particular, the modified drive arm 55 includes a bearing portion 56 that is aligned with the axis of the second offset link housing 34 and an angled portion 57 that is angled toward the longitudinal axis L of the motor. This modified drive arm 55 thus allows the axis A of the working tool to intersect the axis L of the power tool. This modification provides the advantage of an improved depth of cut since the axis of the working tool or blade is shifted closer to the work piece. The orientation of the bearing portion 56 in the modified arm 55 also helps eliminate most of the sliding of the drive arm within the second link housing 34. The modified drive arm 55 moves in the same manner as the drive arm 40.

Figure 10:
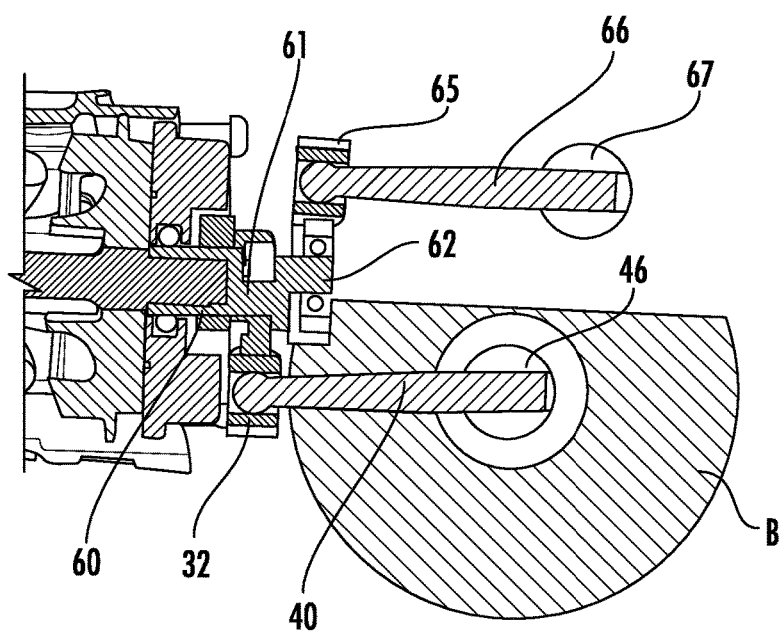
FIG. 10 is a side partial cross-sectional view of an oscillating mechanism having a dual output according to one aspect of the present disclosure.

The oscillating mechanisms described above may be further modified to provide two outputs driven by the same motor. Thus, as shown in FIG. 10, the motor shaft 60 may be configured similar to an automotive crank shaft, with two crank sections 61, 62 that are angularly offset from each other. As shown in FIG. 10, the two crank sections 61, 62 are 180° apart, although other angular orientations are contemplated with appropriate modifications to the housing covering the mechanism. The first crank section 61 engages the link 32 to drive the drive arm 40 for the working tool B. The second crank section 62 may engage a link 65 that is configured similar to the link 32, except that this link drives a second drive arm 66 that oscillates a second hub 67 and associated working tool.

Figure 11:
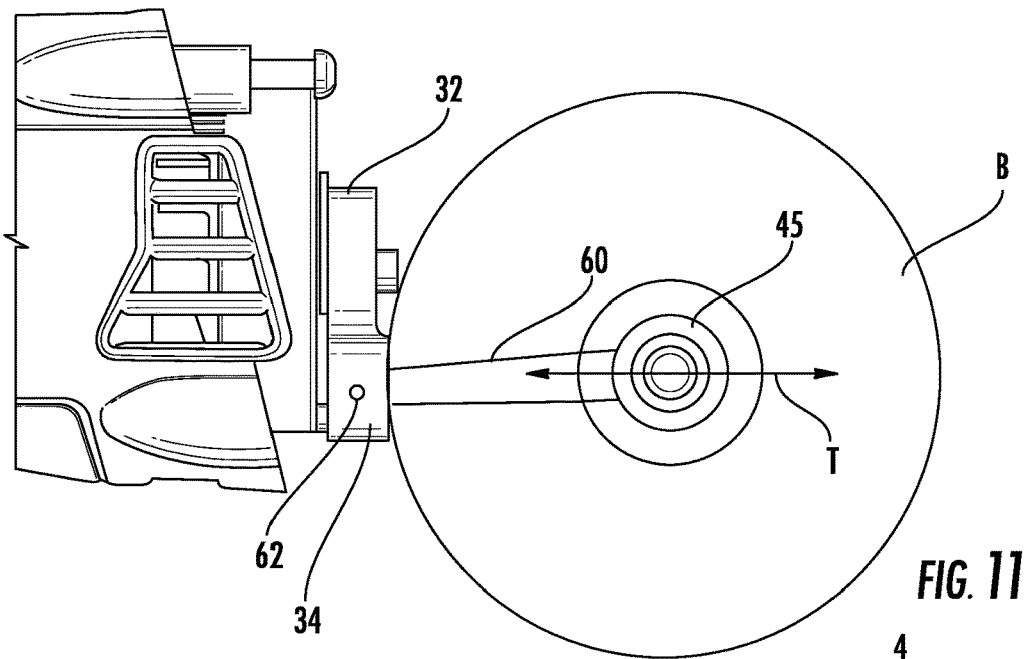
FIG. 11 is a side view of an oscillating and reciprocating mechanism according to a further aspect of the present disclosure.

The oscillating mechanism 30 may be further modified to impart a reciprocating motion to the working tool. As shown in FIG. 11, the drive arm 60 may be modified from the drive arm 40 to replace the spherical end with a pin joint 62. The pin joint allows for relative pivoting between the drive arm and the second link housing 34 but does not allow the end of the drive arm to slide along the axis of the housing. Thus, when the drive arm is moved away from the normal line of action from hub 45 to link 32 the effective length of the drive arm shortens due to the angular offset. This reduction in length pulls and pushes the hub 45 in the direction of the arrow T, thereby imparting a reciprocating motion to the working tool along with the oscillating motion already provided by the mechanism.

Figure 12:
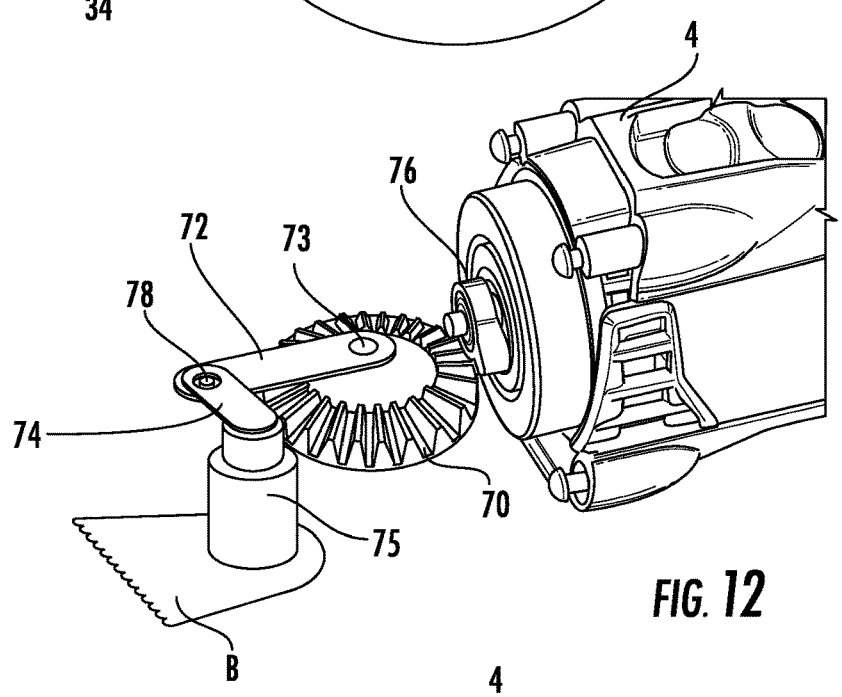
FIGS. 12 and 13 are representations of an oscillating mechanism incorporating a rotating gear driving a pair of links.
Figure 13:
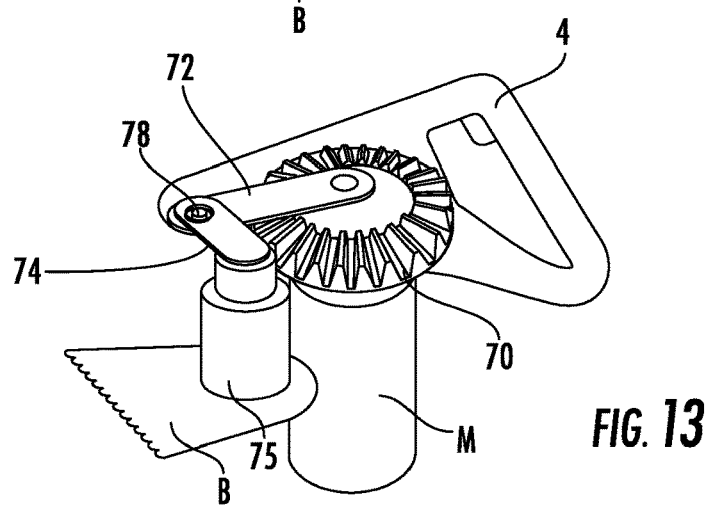

FIGS. 12-13 show a mechanism for imparting oscillating motion that employs a gear 70 driven by the motor M. In FIG. 12 a bevel gear 76 driven by the motor M engages the gear 70 to rotate the gear about an axis that is perpendicular to the axis of the tool and motor. In FIG. 13 the gear 70 is directly driven by the motor, but the motor axis is perpendicular to the hand grip portion H of the power tool. In both configurations, a first link 72 is attached to the gear 70 by a pivot pin 73, and to a second link 74 by a corresponding pin 78. The second link 74 is attached to the hub 75 to which the working tool is mounted. Rotation of the gear 70 thus imparts an oscillating rotation to the hub and working tool.

While the power tool and oscillating mechanism have been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A power tool comprising:
a drive motor having an eccentric drive shaft with an axis of rotation;
a tool holder adapted to support a working tool for oscillating rotational motion; and
an oscillating mechanism disposed between said eccentric drive shaft and said tool holder, said oscillating mechanism including:
an elongated link mounted at one end thereof on said eccentric drive shaft for eccentric movement upon rotation of said drive shaft about said axis of rotation and including on an opposite end thereof a roller bearing having a loose fit with a small amount of play between an inner race and rollers of the bearing, and/or between the rollers and an outer race of the bearing in a radial direction relative to said axis of rotation of said drive shaft; and
an elongated drive arm having;
a first end coupled to said roller bearing of said link in a manner to isolate relative rotation and translation between said link and said drive arm while still imparting an oscillatory motion in one direction to said drive arm; and
a second end engaged to said tool holder to transfer the oscillatory motion to oscillating rotational motion of said tool holder.

2. The power tool of claim 1, wherein:
said link includes an upper link mounted on said eccentric drive shaft and a lower link offset from said upper link, said lower link defining a cylindrical opening; and
said second end of said drive arm is a spherical end slidably disposed within said cylindrical opening to permit relative rotation and axial translation between said drive arm and said lower link.

3. The power tool of claim 2, wherein said lower link includes a cylindrical bushing defining said cylindrical opening.

4. The power tool of claim 2, wherein said lower link includes said roller bearing disposed in said cylindrical opening.

5. The power tool of claim 2, wherein said upper link includes a bearing between said upper link and said eccentric drive shaft.

6. The power tool of claim 2, further comprising a counterweight mounted on said eccentric shaft opposite said lower link.

7. The power tool of claim 1, wherein:
said tool holder includes a central hub supporting the working tool; and
said first end of said drive arm includes a threaded shaft extending through said central hub and a threaded nut for engaging the threaded shaft to fix said drive arm to said central hub.

8. The power tool of claim 1, wherein:
said drive motor defines a longitudinal axis;
said eccentric drive shaft includes an eccentric portion offset from said longitudinal axis; and
said link is mounted on said eccentric portion.

9. The power tool of claim 8, wherein:
said eccentric drive shaft includes an end portion aligned with said longitudinal axis, with said eccentric portion between said motor and said end portion; and
the power tool includes a housing defining a bearing support for supporting said end portion of said eccentric drive shaft.

10. A power tool comprising:
a drive motor having an eccentric drive shaft;
a tool holder adapted to support a working tool for oscillating rotational motion; and
an oscillating mechanism disposed between said eccentric drive shaft and said tool holder, said oscillating mechanism including:
a link mounted on said eccentric drive shaft for eccentric movement upon rotation of said drive shaft; and
an elongated drive arm having;
a first end coupled to said link in a manner to isolate relative rotation and translation between said link and said drive arm while still imparting an oscillatory motion in one direction to said drive arm; and
a second end engaged to said tool holder to transfer the oscillatory motion to oscillating rotational motion of said tool holder, wherein
the drive shaft defines an axis along the length of said drive shaft;
the drive motor defines a longitudinal axis parallel to said axis of the drive shaft;
said tool holder is supported along said longitudinal axis; and
said elongated drive arm is arranged at an angle between said link and said tool holder, said angle being non-parallel and non-perpendicular to said longitudinal axis.

11. A power tool comprising:
a drive motor having an eccentric drive shaft;
a tool holder adapted to support a working tool for oscillating rotational motion; and
an oscillating mechanism disposed between said eccentric drive shaft and said tool holder, said oscillating mechanism including:
a link mounted on said eccentric drive shaft for eccentric movement upon rotation of said drive shaft; and
an elongated drive arm having;
a first end coupled to said link in a manner to isolate relative rotation and translation between said link and said drive arm while still imparting an oscillatory motion in one direction to said drive arm; and
a second end engaged to said tool holder to transfer the oscillatory motion to oscillating rotational motion of said tool holder, wherein
said eccentric drive shaft includes two eccentric portions;
said link is mounted to one of said two eccentric portions; and
a second link is mounted to the other of said two eccentric portions, said second link coupled to a second drive arm for another working tool.

12. An oscillating mechanism for a power tool, the oscillating mechanism engaged between an eccentric drive shaft of the power tool and a tool holder adapted to support a working tool for oscillating rotational motion, the drive shaft having an axis of rotation, the oscillating mechanism comprising:
an elongated link mounted at one end thereof on said eccentric drive shaft for eccentric movement upon rotation of said drive shaft about said axis of rotation and including on an opposite end thereof a roller bearing having a loose fit with a small amount of play between an inner race and rollers of the bearing, and/or between the rollers and an outer race of the bearing in a radial direction relative to said axis of rotation of said drive shaft; and
an elongated drive arm having;
a first end coupled to said roller bearing of said link in a manner to isolate relative rotation and translation between said link and said drive arm while still imparting an oscillatory motion in one direction to said drive arm; and
a second end engageable to the tool holder to transfer the oscillatory motion to oscillating rotational motion of said tool holder.

13. The oscillating mechanism of claim 12, wherein:
said link includes an upper link mountable on the eccentric drive shaft and a lower link offset from said upper link, said lower link defining a cylindrical opening; and
said second end of said drive arm is a spherical end slidably disposed within said cylindrical opening to permit relative rotation and axial translation between said drive arm and said lower link.

14. The oscillating mechanism of claim 13, wherein said lower link includes a cylindrical bushing defining said cylindrical opening.

15. The oscillating mechanism of claim 13, wherein said lower link includes a roller bearing having a loose fit with a small amount of play between the inner race and the rollers of the bearing, and/or between the rollers and the outer race of the bearing.

16. The oscillating mechanism of claim 13, wherein said upper link includes a bearing mountable on the eccentric drive shaft.

17. The oscillating mechanism of claim 13, further comprising a counterweight mountable on said eccentric shaft opposite said lower link.

* * * * *